(12) United States Patent
Takeya et al.

(10) Patent No.: US 6,171,552 B1
(45) Date of Patent: Jan. 9, 2001

(54) HYDRIDE FORMATION ANALYTICAL APPARATUS

(75) Inventors: Minoru Takeya; Yutaka Hayashibe; Kazutoshi Shimura, all of Omiya (JP)

(73) Assignee: Mitsubishi Materials Corporation, Tokyo (JP)

( * ) Notice: Under 35 U.S.C. 154(b), the term of this patent shall be extended for 0 days.

(21) Appl. No.: 09/016,416

(22) Filed: Jan. 30, 1998

(30) Foreign Application Priority Data

Jan. 30, 1997 (JP) .................................................. 9-016425

(51) Int. Cl.[7] .................................................. G01N 33/20
(52) U.S. Cl. .............................. 422/68.1; 422/80; 436/73; 436/77; 436/81; 436/84; 436/181; 436/182
(58) Field of Search ..................... 422/68.1, 80; 436/73, 436/77, 81, 84, 181, 182

(56) References Cited

U.S. PATENT DOCUMENTS

| | | | |
|---|---|---|---|
| 4,230,665 | * | 10/1980 | Huber . |
| 5,055,409 | * | 10/1991 | Astrom . |
| 5,314,664 | * | 5/1994 | Sperling et al. . |
| 5,741,710 | * | 4/1998 | Ek . |
| 5,792,663 | * | 8/1998 | Fry et al. . |
| 5,939,648 | * | 8/1999 | Phan .................................. 73/864.81 |

OTHER PUBLICATIONS

Analytical Abstracts accession No.: 56–09–H–00111, Xu Et Al., Fenxi Shiyanshi vol. 13, Issue 2, pp. 20–22, Published Mar. 1994.

* cited by examiner

*Primary Examiner*—Jan Ludlow
(74) *Attorney, Agent, or Firm*—Oblon, Spivak, McClelland, Maier & Neustadt, P.C.

(57) ABSTRACT

The present invention provides for a hydride formation analytical apparatus which forms hydrides of target components contained in a sample liquid and then analyzes them. The hydride formation analytical apparatus comprises a sample-introducing part, a reagent-introducing part, a reaction part, a gas-liquid separating part and a detecting part, wherein an acid-feeding part and a reducing agent-feeding part are part of the reagent-introducing part; the hydride gas of the sample is formed by the aid of the acid and the reducing agent fed into the above reaction part; and this is introduced into the detecting part for analysis.

16 Claims, 3 Drawing Sheets

HYDRIDE FORMATION ANALYTICAL APPARATUS

BACKGROUND OF THE INVENTION

1. Field of the Invention

The present invention relates to an analytical apparatus that forms and analyzes the hydrides of target components contained in a sample.

2. Description of the Related Art

Atomic absorption and ICP atomic emission analysis techniques are widely used in analytic chemistry laboratories for measuring the concentrations of various elements in a sample. One preferred procedure for performing this analysis is to first decompose the sample into gas phase hydrides then atomize these hydrides in the detecting part of an atomic absorption or ICP atomic emission apparatus, and finally measure the concentrations of selected elements from the sample. Converting the original sample into gas phase hydrides make the target elements much easier to atomize and detect by atomic absorption/emission techniques.

The hydrides are formed preferably by adding acids and reducing agents to the samples. The types and concentrations of acids and reducing agents used to form the hydrides depend upon the elements that are analyzed. Unfortunately, selecting the types and concentrations of the hydride forming agents has, up to now, been a time consuming, manual operation. Every time a new element was measured in a sample, manual adjustments had to be made to the types and concentrations of hydride forming agents.

The concentration of an element from a sample is measured by comparing the spectral intensity of an atomic absorption or emission line with the intensity of that same line from a standard that contains a known concentration of the same element. The intensities of the atomic absorption/emission line are plotted as a function of the concentration of the standard, and the resulting curve of intensity vs. elemental concentration is called the analytical curve.

When the concentration of an element in a sample is too high or too low to fall within the upper and lower concentration limits of the analytical curve, the measurement must be repeated under different hydride formation conditions. Up to now, these adjustments were made by hand by the operator of the apparatus.

Further, conventional apparatuses employ mainly a continuous suction method, a batch addition method and an FIA method (loop injection method) as methods for introducing samples. The continuous suction method requires a lot (at least about 20 ml) of sample liquids, and therefore the concentration rate is restricted, which in turn restricts analysis of trace amounts. The batch addition method makes use of an air segment system, and therefore the sample liquids remain in the tube line to allow the memory to remain. Accordingly, the tube line has to be washed every measurement.

SUMMARY OF THE INVENTION

Accordingly, one object of the present invention is to provide for a hydride formation analytical apparatus that automatically adjusts the type and concentrations of reagents, preferably of hydride forming reagents, when analyzing one or more elements in a sample. Another object of the invention provides for a hydride formation analytical apparatus that automatically introduces a sample into the apparatus, preferably forms hydrides of elements in the sample, and performs an elemental analysis on the hydrides.

A further object of the invention provides for a hydride formation analytical apparatus that automatically adjusts the types and concentrations of reagents, preferably hydride forming reagents, to keep the sample element concentration within the upper and low concentration limits of a standard analytical curve.

These and other objects of the present invention have been satisfied by the development of a hydride formation analytical apparatus.

The apparatus of the present invention reduces the concentration of residual sample materials preferably below a detectable level, by transporting a sample liquid, preferably with a carrier liquid instead of an air segment. The apparatus also preferably uses an amount of sample liquid small enough to permit measurements at elevated concentrations of the sample. The amount of sample liquid used by the apparatus for a measurement is preferably less than 5 ml, more preferably less than 1 ml. The apparatus of the present invention also preferably provides a means capable of controlling an acid concentration and a reducing agent concentration in an acid-feeding part and a reducing agent-feeding part that form part of a sample-introducing part to permit the control of these concentrations based on the kinds of samples analyzed. The apparatus preferably further comprises a control circuit for controlling integrally the respective parts to permit the automation of a series of operations extending from the introduction of the sample liquid through the analysis thereof.

The present invention preferably provides for a hydride formation analytical apparatus preferably comprising a sample-introducing part, a reagent-introducing part, a reaction part, a gas-liquid separating part and a detecting part which are continuously connected via tube lines. A sample liquid holding part, preferably a loop, is located in the sample-introducing part to introduce the sample liquid into the reaction part via the tube line preferably by the aid of a carrier. The reagent-introducing part is connected to the reaction part. An acid-feeding part and a reducing agent-feeding part are preferably components of the reagent-introducing part. The hydride gases formed from target elements in the sample are made by reacting the acid and reducing agents with the sample liquid, preferably in the reaction part. The mixture of the sample liquid and hydride gases are introduced into the gas-liquid separating part preferably from the reaction part, to separate the gases from the liquid. Preferably, inert gas is also introduced into the above gas-liquid separating part to aid in the hydride gas separation process. The separated hydride gases are preferably introduced into the detecting part where they are analyzed.

The analytical apparatus of the present invention preferably includes a preliminary reducing agent-introducing part as well as the acid-feeding part and the reducing agent-feeding part located in the reagent-introducing part. The acid and the reducing agent are preferably fed after the preliminary reagent is fed to the sample liquid in the reaction part.

The analytical apparatus of the present invention preferably further comprises a means capable of selecting the concentrations of the acid and the reducing agent. Preferably this includes an analytical apparatus in which the acids having different concentrations are held in the acid-feeding part, and the concentrations of the acids are selected based on the type of sample liquid. Preferably, this also includes an analytical apparatus in which the reducing agents having different concentrations are held in the reducing agent-feeding part, and the concentrations of the reducing agents are selected based on the type of sample liquid. The analytical apparatus of the present invention preferably includes a feeding means for the acid and diluting water located in the acid-feeding part, wherein the acid concentration is controlled by the relative portions of acid and diluting water fed into the reaction part. Likewise, an analytical apparatus of the present invention preferably provides for a feeding means for the reducing agent and diluting water, wherein the reducing agent concentration is controlled by the relative portions of reducing agent and diluting water fed into the reaction part.

The analytical apparatus of the present invention also preferably comprises a plurality of preliminary reducing agents held in the preliminary reducing agent-introducing part, and selected based on the types of sample liquids analyzed. The apparatus also preferably includes a control circuit for controlling integrally the actions of the sample-introducing part, the reagent-introducing part, the reaction part, the gas-liquid separating part and the detecting part. This control circuit permits the automation of operations extending from the introduction of the sample liquid through the analysis thereof.

DESCRIPTION OF THE PREFERRED EMBODIMENTS

Figure 1:
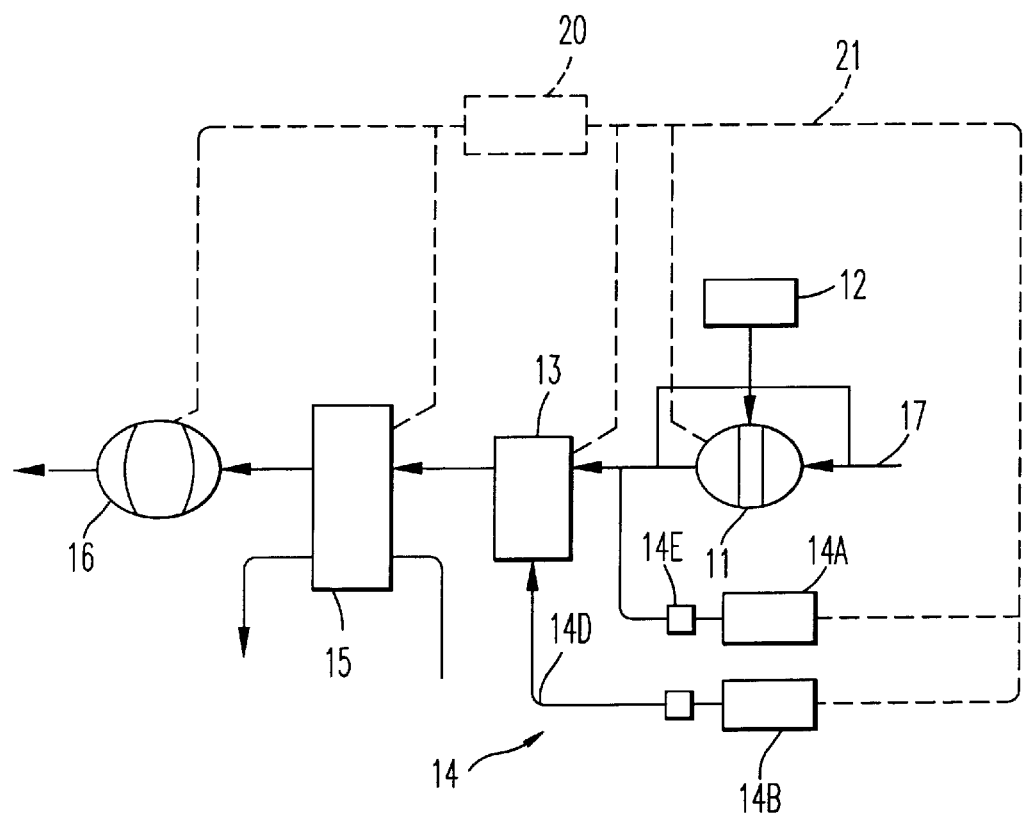
FIG. 1 is a schematic drawing showing a preferred embodiment of the apparatus of the present invention.

As shown in FIGS. 1–4, the analytical apparatus of the present invention is preferably a continuous flow analytical apparatus comprising a sample-introducing part 11, a reaction part 13, a reagent-introducing part 14, a gas-liquid separating part 15 and a detecting part 16 that are preferably connected via tube lines 17. In one preferred embodiment, the apparatus is based on flow injection (FI): hydride forming reagents are added to the reaction part while a sample liquid flows through the tube line. The sample liquid is then introduced into the reaction part to react with the hydride forming agents and the resulting hydrides of the sample are introduced into the detecting part for analysis.

In another preferred embodiment, the sample-introducing part 11 has with a shut-off valve interposed by the tube line in the measuring system, and a loop for holding the sample liquid is installed in the above shut-off valve. The shut-off valve is preferably a hexagonal valve. The shut-off valve is preferably located in the switching part of the tube line (17). In yet another preferred embodiment, the autosampler 12 may be connected to the loop holding the sample liquid so that fixed amounts of this liquid are automatically introduced into the loop.

When the shut-off valve is opened to the tube line 17, the sample liquid contained in the loop is preferably introduced into the tube line by a carrier flowing through the above tube line and then introduced into the reaction part.

Preferred examples of the reaction part include forming the tube line 17 into a coil so that reaction time is secured.

The reagent-introducing part 14 is connected to the above reaction part 13, and the reaction of the sample liquid with the reagent occurs while the sample liquid and hydride forming reagents flow through the reaction part 13.

An acid-feeding part 14a and a reducing agent-feeding part 14b are located in the reagent-introducing part, and these feeding parts connect to the reaction part 13 through a feeding tube line 14d. The acid and the reducing agent introduced into the reaction part through tube line 14d preferably react with a target compounds in the sample liquid to form hydrides of the sample liquids.

The hydride forming reagents preferably comprise an acid and a reducing agent. When the acid is mixed with the sample liquid it generates ions from components of the sample liquid and hydrogen. The reducing agent reacts with these ions in the presence of hydrogen to form hydrides of the sample components.

The selection of acids and the reducing agents are based on the kinds of analysis target elements and the properties of the sample liquid. Preferably, hydrochloric acid is used as the acid for analysis of metallic elements, and sodium boron hydride ($NaBH_4$) is used as the reducing agent for these elements.

Figure 2:
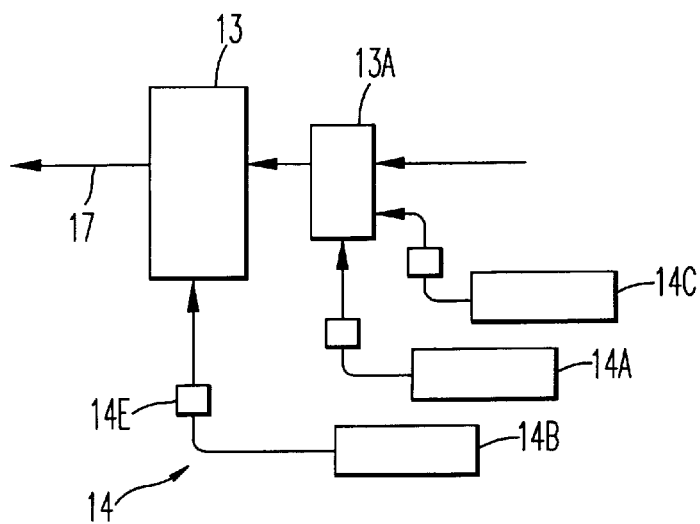
FIG. 2 is a schematic drawing showing a preferred embodiment of the reagent-introducing part.

FIG. 2 shows a preferred embodiment where a preliminary reducing agent-feeding part is preferably located in the reagent-introducing part described above together with the acid-feeding part 14a and the reducing agent-introducing part 14b. In another preferred embodiment, a preliminary reaction part 13a is located near the reaction part 13. The preliminary reducing agent-feeding part 14c and the acid-feeding part 14a described above are preferably connected to this preliminary reaction part 13a to feed the preliminary reducing agent and the acid to the sample liquid in the preliminary reaction part 13a. The preliminary reducing agent reacts with the sample liquid to reduce an ion from a higher to lower oxidation state. Preferred examples include reducing arsenic (As) from pentavalent to trivalent state and selenium (Se) from hexavalent to tetravalent state. Preliminary reducing agents are preferred when an ion can be reduced to a lower oxidation state that more easily converts to a hydride. The sample liquid treated with the preliminary reducing agent is introduced into the reaction part 13 and the reducing agent is added to form the hydrides. Preferred preliminary reducing agents include potassium iodide for the reduction of arsenic.

A means for controlling the concentrations of the acid and the reducing agent is preferably located in the acid-feeding part 14a and the reducing agent-feeding part 14b described above, and a means for controlling the concentration of preliminary reducing agents is located in the preliminary reducing agent-feeding part 14c.

Figure 3:
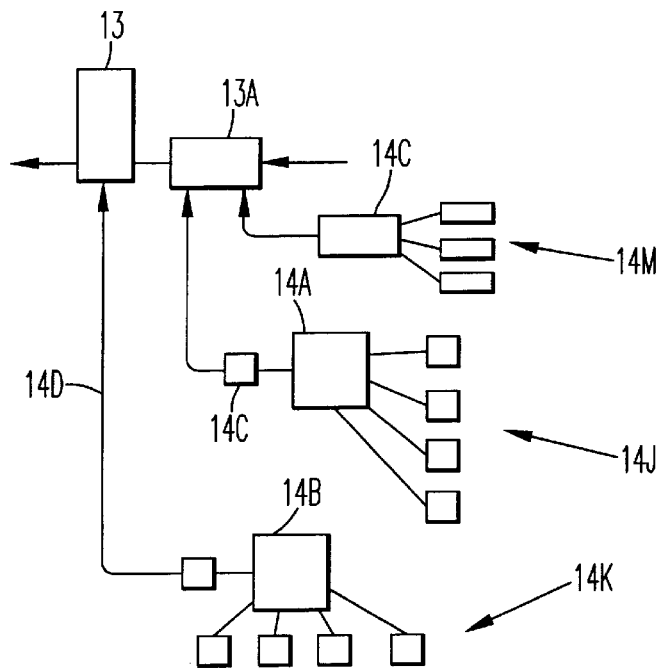
FIG. 3 is a schematic drawing showing another preferred embodiment of the reagent-introducing part.
Figure 4:
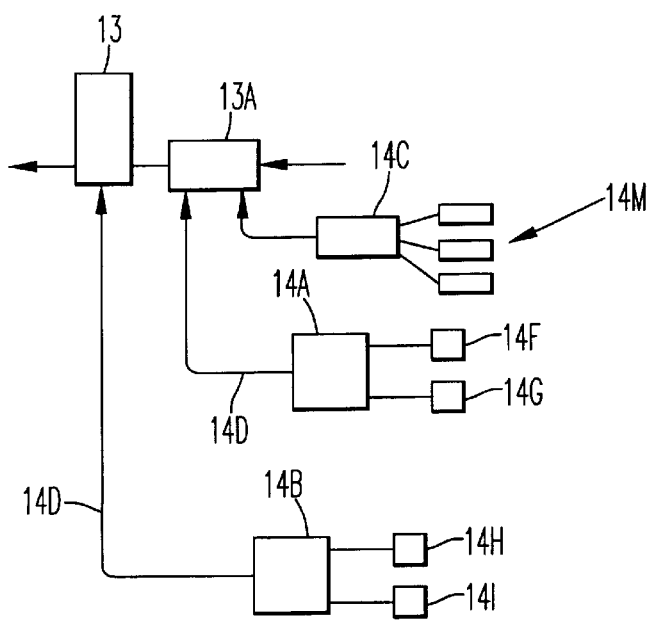
FIG. 4 is a schematic drawing showing yet another preferred embodiment of the reagent-introducing part.

FIG. 3 shows a preferred embodiment where the vessels 14j, 14k contain acids and reducing agents having different concentrations. The vessels are located in the acid-feeding part 14a and the reducing agent-feeding part 14b. In the preferred example shown in FIG. 3, four concentration levels of hydrochloric acid 1M, 2M, 4M and 6M and four concentration levels of sodium boron hydride 0.5%, 1.0%, 2.0% and 5.0% are provided. These concentrations are selected according to the condition of the sample liquid. They are preferably sent to the reaction part 13 or the preliminary reaction part 13a through a feeding pump 14e and the tube line 14d. FIG. 4 shows another embodiment for controlling the concentrations of the hydride forming agents. The acid-feeding part 14a is formed by a feeding pump 14f for feeding concentrated acid and a feeding pump 14g for feeding diluting water. The reducing agent-feeding part 14b is formed by a feeding pump 14h for feeding the reducing agent having a high concentration and a feeding pump 14i for feeding diluting water. The amounts of diluting water added to the acid and the reducing agent are controlled to dilute the acid and the reducing agent to the prescribed concentrations. After diluting to the proper concentrations, the hydride forming agents are fed into the reaction part 13 through the tube line 14d.

Further, plural vessels 14m holding various reducing agents respectively are disposed in the preliminary reducing agent-feeding part 14c, and these reducing agents are suitably selected according to the sample liquids. In one preferred example, hydrogen peroxide, potassium iodide and water are held in the respective vessels as the preliminary reducing agents.

The gas-liquid separating part 15 is a closed vessel into which inert gas is fed together with the sample liquid containing the hydrides, and an inert gas-feeding tube line 15a and a tube line 15b for discharging a waste liquid to the outside are connected thereto together with the tube line 17 in the measuring system. The tube line 17 in the measuring system connects to the detecting part 16, and hydride gas from the gas-liquid separating part is introduced into the detecting part 16 through the tube line 17.

In a preferred embodiment, an atomic absorption spectrophotometer or an ICP emission spectral analyzer is disposed in the detecting part 16 to analyze the target elements that are introduced in the form of the hydrides.

In the preferred embodiments of analytical apparatuses described above, the sample-introducing part 11, the respective parts of the reagent-introducing part 14 (the acid-introducing part, the reducing agent-introducing part and the preliminary reducing agent-introducing part), the reaction part 13 and the gas-liquid separating part 15 and the detecting part 16 are preferably connected by a control circuit 21, and the actions of these respective parts are automatically controlled by a computer disposed in a control part 20. The control circuit 20 and computer preferably execute a series of operations that permit the introduction, hydride formation and analysis of target compounds in a sample to be automatically carried out.

Figure 5:
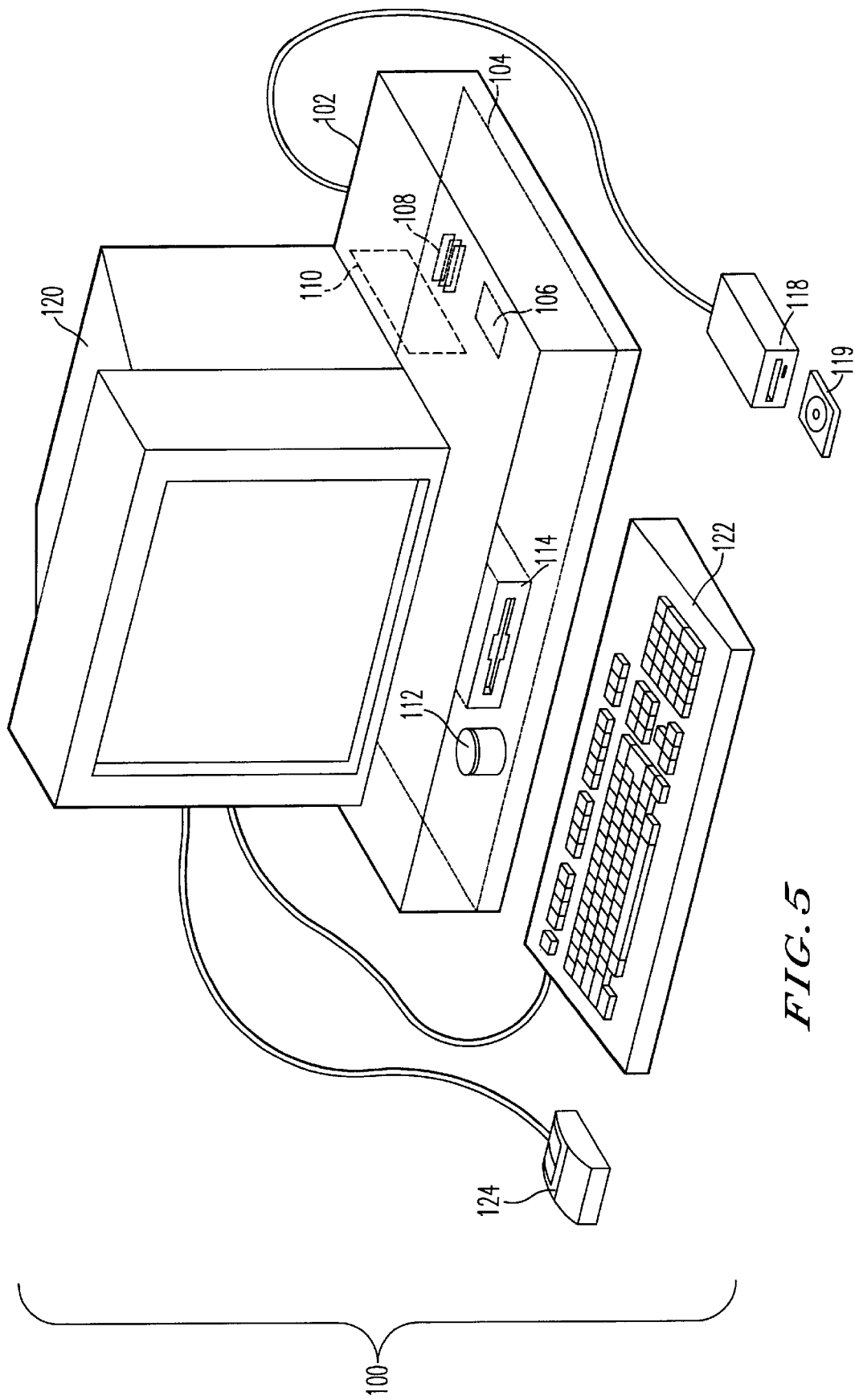
FIG. 5 is a schematic drawing showing a preferred embodiment of a computer that may be used with the apparatus of the present invention.

FIG. 5 shows a schematic illustration of a computer system which may be connected to the control circuit 20 of the present invention. The computer 100 comprises a computer housing 102 housing a motherboard 104 which contains a CPU 106, memory 108 (e.g. DRAM, ROM, EPROM, EEPROM, SRAM and Flash RAM), and other optional special purpose logic devices (e.g., ASICs) or configurable logic devices (e.g. GAL and reprogrammable FPGA). The computer 100 also includes plural input devices, (e.g. a keyboard 122 and mouse 124), and a display card 110 for controlling monitor 120. In addition, the computer system 100 further includes a floppy disk drive 114; other removable media devices (e.g., compact disc 119, tape, and removable magneto-optical media (not shown)); and a hard disk 112, or other fixed, high density media drives connected using an appropriate device bus (e.g., a SCSI bus or an Enhanced IDE bus). Although compact disc 119 is shown in a CD caddy, the compact disc 119 can be inserted directly into CD-ROM drives which do not require caddies. Also connected to the same device bus or another device bus as the high density media drives, the computer 100 may additionally include a compact disc reader 118, a compact disc reader/writer unit (not shown) or a compact disc jukebox (not shown). In addition, a printer (not shown) also provides printed listings of the measurement data from the apparatus.

The system further includes at least one computer readable media. Examples of such computer readable media are compact discs 119, hard disks 112, floppy disks, tape, magnet-optical disks, PROMs (EPROM, EEPROM, Flash EPROM), DRAM, SRAM, etc. Stored on any one or on a combination of the computer readable media, the present invention includes software for controlling both the hardware of the computer 100 and for enabling the computer 100 to interact with a human user. Such software may include, but is not limited to, device drivers, operating systems and user applications, such a development tools. Such computer readable media further includes a computer program product of the present invention for controlling at least one task performed by at least one of the parts of the hydride formation analytical apparatus of the present invention.

In a preferred embodiment, the series of operations automatically carried out include selecting the acid concentration, the reducing agent concentration and the preliminary reducing agent, if used, based on the kinds of the analysis target elements and the properties of the sample liquid. In another preferred embodiment, the selection of the hydride forming reagents are input into the computer by an operator. The acid and the reducing agent having a computer controlled concentrations are preferably prepared by controlling the ratio of diluting water and concentrated hydride forming reagents that are fed into the reaction part or preliminary reaction part of the apparatus.

EXAMPLES

Having generally described this invention, a further understanding can be obtained by reference to certain specific examples which are provided herein for purposes of illustration only and are not intended to be limiting unless otherwise specified. All percentages are by weight unless otherwise stated.

The examples according to the apparatuses of the present invention shall be shown below. An atomic absorption spectrophotometer is used as a detector in the present examples to explain the measuring examples of arsenic.

Example 1

An apparatus whose schematic is shown in FIG. 3 is started according to the following procedure:

(a) The measuring system is started, and the fixed amount of water is sent to the tube line 17 with water used as a carrier to wash the inside of the tube line. Then, the auto-sampler 12 and attached valves are initialized, is argon introduced into the gas-liquid separating part 15.

(b) The detecting part 16 is started: preliminary calibration of the atomic absorption spectro-photometer is performed, the hollow cathode lamp installed in the spectro photometer is preheated as well as the heating of a tube furnace.

(c) The measuring conditions are inputted from a controlling computer to set up the position and the concentration of a standard liquid on the auto-sampler, the number and types of the respective sample liquids and the repetitive measuring frequency of the respective sample liquids. The computer will automatically select the kinds of the reagents ($NaBH_4$ and $HCl$), the kinds of the preliminary reducing agents, the flow amounts of these respective reagents, the optimum concentrations of the reagents, the flow amount of the carrier, the flow amount of argon gas, the temperature of a reaction bath, the temperature of the tube furnace for atomizing the analyte, and the quantitative lower limit concentration or absorbance.

(d) The information of the measurement target elements are inputted to the controlling computer. When plural elements are measured, all elements are designated and inputted. Hereinafter, the operation of the apparatus will be described for analyzing a sample containing arsenic as the target compound. Obviously, numerous other target compounds may be used with the apparatus of the present invention.

(e) In measuring arsenic. 3M hydrochloric acid as the acid, 1% $NaBH_4$ as the reducing agent and a 40% KI solution as the preliminary reducing agent are automatically designated as the standard conditions from the computer. The reagents described above are selected in the acid-feeding part, the reducing agent-feeding part and the preliminary reducing agent-feeding part according to this designation and automatically fed into the preliminary reaction part and the reaction part in a proportion of 2 ml/min respectively.

(f) This condition is maintained for prescribed time (for example, 3 minutes) to stabilize the measuring system. In addition, the hollow cathode lamp is set in an optimum position on a measuring optical path, and the measuring wavelength is automatically set to a resonance line wavelength having a maximum sensitivity for arsenic (193.7 nm).

(g) After the measuring system is stabilized, the standard liquid and the sample liquids are measured in succession. The sample liquids are introduced in an amount of 500 ul into the measuring system by the aid of a carrier (water and the like) in the sample-introducing part. After measuring the respective sample liquids, the absorbances are calculated (peak height or peak area), and the concentrations of the measured elements contained in the sample liquids are calculated based on the measured absorbances. The results are shown on a display device connected to the control part and recorded in a computer memory area of the control part.

(h) The computer determines if the sample concentration is within the upper and lower concentration limits of the standard analytical curve. If not, the computer instructs the apparatus to remeasure the sample liquid. For example, if the samples of the high concentrations exceed the range of the analytical curve:

(1) The measurement is rerun with half (250 µl) of the amount of sample used in the first measurement.

(2) If the sample concentration is still measured above the upper limit of the analyte curve, the concentration is reduced by half again (250 µl) and another measurement is made.

(3) This process of halving the concentration of sample and remeasuring will continue for several more times until the sample measurement falls within the concentration range measured by the standard analytical curve.

(4) If the sample concentration still exceeds the upper limit of concentration on the analytical curve after several cycles of cutting the sample concentration in half, then the computer starts to lower the concentration of acid used to decompose the sample liquid. If this measured concentration falls within the range of the analytical curve, the standard liquid having the maximum concentration is measured again with the same acid concentration to determine a desensitizing factor (D), and the calculated concentration of the analysis target element contained in the sample is multiplied by this factor to carry out the determination.

(5) When the measured concentration still exceeds the range of the analytical curve even by controlling the acid concentration in the above manner, the sample and the hydrochloric acid concentrations are maintained, and the concentration of the reducing agent lowered to in successive measurements. If the measured sample now falls within the range of the analytical curve, the standard liquid having the maximum concentration is measured again with the same reducing agent concentration to determine a desensitizing factor (D), and the calculated concentration of the analysis target element contained in the sample is multiplied by this factor to carry out the determination.

(6) Finally, when the measured concentration still does not fall within the range of the analytical curve, a note is added to the data indicating the sample measurement exceeded the upper limit of concentration of the standard, then the next measurement is carried out.

(i) Another situation where samples require remeasurement, include samples measured at concentrations lower than the lower limit of the analyte curve. In this situation, the samples are remeasured as follows:

(1) The injection amount of the sample is increased to double (1000 µl), and the pertinent sample liquids are remeasured.

(2) If the measured sample concentration is still below the lower limit of the analytical curve, the injection amount of the sample is maintained at the highest level, and acid having a higher concentration is selected to continue the measurement. This is repeated up to the maximum concentration of the acid.

(3) When the measured concentration is still below the lower limit, the injection amount of the sample and acid concentrations are maintained at their highest levels, and a higher concentration of reducing agent is selected to continue the measurement. This is repeated until the highest reducing agent concentration is reached.

(4) Finally, when the measured concentration still does not fall within the range of the analytical curve, a note is added to the data indicating the sample measurement did not reach the lower limit concentration of the standard, and then the next measurement is carried out.

When more than one target element is measured by the apparatus, the measuring conditions are set up for each element to carry out the measurement in order. If the changed measuring conditions are inputted in advance to the computer, the multiple element analysis can be completely automated.

Example 2

An apparatus whose schematic is shown in FIG. 4 was started according to the following procedure:

(a) The condition of the measuring system was set up in the same manner as in (a) to (d) of Example 1.

(b) In the analysis of arsenic, the flow amounts in the respective feeding pumps were adjusted so that the optimum reagent concentrations were obtained. For example, the ratio of the flow amount in the feeding pump 14h to that in the feeding pump 14i for the reducing agents was set at 1:6, and 1% NaBH$_4$ was sent to the reaction part 13 through the tube line 14d. In this case, the total flow amount in the tube line 14d was controlled to 2 ml/minute (to be specific, the flow amount of the reducing agent: 0.29 ml/minute and the flow amount of diluting water: 1–71 ml/minute).

(c) Similarly, the ratio of the flow amount in the feeding pump 14f to that in the feeding pump 14g was set at 1:2, and 6M HCl was sent at 2 ml/minute through the tube line 14d.

(d) Further, a 40% KI solution which was the preliminary reducing agent was sent to the preliminary reaction part 13a at 2 ml/minute.

(e) This condition was maintained for prescribed time (for example. 3 minutes) to stabilize the apparatus condition. Meanwhile, the hollow cathode lamp was set in an optimum position on a measuring optical path, and the measuring wavelength was automatically set up to a resonance line wavelength for the maximum sensitivity of arsenic (193.7 nm).

(f) After the measuring system was stabilized, the standard liquid and the sample liquids were measured in succession. The sample liquids were introduced in an amount of 500 μl into the measuring system by the aid of a carrier (water and the like) on the standard conditions in the sample-introducing part. After measuring the respective sample liquids, the absorbances were calculated (peak height or peak area), and the concentrations of the measured elements contained in the sample liquids were calculated based on the measured absorbances. The results were shown on a display device connected to the control part and recorded in the memory of the control part.

(g) If it was determined that the concentration of sample was outside the upper or lower concentration limits of the analytical curve, then the sample was measured under new conditions. The mariner for the remeasurement was fundamentally the same as for Example 1, except that the acid concentration and the reducing agent concentration were adjusted by controlling the flow amounts in the feeding pumps.

For example, for the very high sample concentrations, the amount of diluting water was increased to lower the concentrations of the acid and the reducing agent by half, and the remeasurement is carried out. The concentrations of the acids and reducing agents were changed by varying the amount of the acid or agent, or by varying the amount of diluting water added to the acid or agent or by varying both components.

Example 3

A preferred embodiment of the present invention whose schematic is shown in FIG. 3 was used to measure arsenic. An arsenic standard liquid was used to prepare an analytical curve, and the analytical curve fell in a linear range (dynamic range) of 0.03 to 0.2 ppm (absorbance: 0.030 to 0.250). In this case, the measurement was carried out under standard conditions (sample injection amount—500 μl, hydrochloric acid concentration: 3M and sodium boron hydride: 1%). The results obtained by the automated measuring of the sample liquids having various arsenic concentrations are shown in Table 1. The measurement was carried but in order of the measuring numbers. The mark "-" in the absorbance column means the omission of the measurement, and N. D. means arsenic was not present at measurable levels. Further, OV showed deviation from the measuring range. The measuring system in the present invention was set up so that the respective hydrochloric acid solutions had concentrations of 1, 2, 3 and 6M and the respective sodium boron hydride solutions had concentrations of 0.5, 1.0, 2.0 and 5.0% by weight.

TABLE 1

Arsenic analytical result according to the measuring system shown in FIG. 3

| | Measuring conditions | | | | | | |
|---|---|---|---|---|---|---|---|
| Measuring No. | Sample injection amount (μm) | Hydrochloric acid concentration (M) | NaBH$_4$ % | Peak height/arsenic | | | |
| | | | | 0.001 | 0.01 | 0.1 | 1 |
| 1 | 500 | 3 | 1 | N.D. | N.D. | 0.121 | OV. |
| 2 | 250 | 3 | 1 | — | — | — | OV. |
| 3 | 125 | 3 | 1 | — | — | — | 0.28 |
| 4 | 63 | 3 | 1 | — | — | — | 0.143 |
| 5 | 63 | 2 | 1 | — | — | — | — |
| 6 | 63 | 1 | 1 | — | — | — | — |
| 7 | 63 | 1 | 0.5 | — | — | — | — |
| 8 | 1000 | 3 | 1 | N.D. | 0.009 | — | — |
| 9 | 1000 | 6 | 1 | N.D. | 0.034 | — | — |
| 10 | 1000 | 6 | 2 | N.D. | — | — | — |
| 11 | 1000 | 6 | 5 | N.D. | — | — | — |

Example 4

The schematic of the apparatus used to measure arsenic in this example is shown in FIG. 4. An arsenic standard liquid was used to prepare an analytical curve, and as a result thereof, the analytical curve fell in a linear range (dynamic range) of 0.03 to 0.2 ppm absorbance: 0.030 to 0.250). In this case, the measurement was carried out under standard conditions (sample injection a-mount: 500 μl, hydrochloric acid concentration: 3M and sodium boron hydride: 1%). The results obtained the automated measuring of the sample liquids having various arsenic concentrations are shown in Table 2. The measurement was carried out in order of the measuring numbers. The mark "-" in the absorbance column means the omission of the measurement, and N. D. means arsenic was not present at measurable levels. Further, OV shows deviation from the measuring range. The measuring system in the present invention was set up so that a hydrochloric acid solution had a concentration of 12M and a sodium boron hydride solution had a concentration of 5.0%.

TABLE 2

Arsenic analytical result according to the measuring system shown in FIG. 4

| Measuring No. | Sample injection amount | Hydrochloric acid concentration | 14f ml/min | 14g ml/min | 14h ml/min | 14i ml/min | NaBH$_4$ % | Peak height/arsenic | | | |
|---|---|---|---|---|---|---|---|---|---|---|---|
| | | | | | | | | 0.001 | 0.01 | 0.1 | 1 |
| 1 | 500 | 3M | 0.67 | 1.33 | 0.4 | 1.6 | 1 | N.D. | N.D. | 0.121 | OV. |
| 2 | 250 | 3 | 0.67 | 1.33 | 0.4 | 1.6 | 1 | — | — | — | OV. |
| 3 | 125 | 3 | 0.67 | 1.33 | 0.4 | 1.6 | 1 | — | — | — | 0.28 |
| 4 | 63 | 3 | 0.67 | 1.33 | 0.4 | 1.6 | 1 | — | — | — | 0.143 |
| 5 | 63 | 2 | 0.44 | 1.56 | 0.4 | 1.6 | 1 | — | — | — | — |
| 6 | 63 | 1 | 0.22 | 1.78 | 0.4 | 1.6 | 1 | — | — | — | — |
| 7 | 63 | 1 | 0.22 | 1.78 | 0.2 | 1.8 | 0.5 | — | — | — | — |
| 8 | 1000 | 3 | 0.67 | 1.33 | 0.4 | 1.6 | 1 | N.D. | 0.009 | — | — |
| 9 | 1000 | 5 | 1 | 1 | 0.4 | 1.6 | 1 | N.D. | 0.034 | — | — |
| 10 | 1000 | 6 | 1 | 1 | 0.8 | 1.2 | 2 | N.D. | — | — | — |
| 11 | 1000 | 6 | 1 | 1 | 2 | 2 | 5 | N.D. | — | — | — |

In Tables 1 and 2, the samples having arsenic concentrations on the order of 0.01 ppm were measured according to the conditions of Example 1 to find that they fell below the detection limit. Accordingly, the measurement was continued with the sample injection amount increased to double (1000 μl) to find that a measured value of 0.009 was obtained (Measuring No. 8). However, this fell in a range below the analytical curve lower limit, and therefore the measurement was further continued with the hydrochloric acid concentration increased to double (6M) to find that a measured value of 0.034 was obtained (Measuring No. 9).

The sample having an arsenic concentration of a 0.1 ppm order could be measured within a range of the analytical curve on the conditions of Measuring No. 1.

The samples having an arsenic concentration of a 1 ppm order exceeded the analytical curve limit on the conditions of Measuring No. 1 and 2, but a measured value of 0.28 was obtained on the conditions of Measuring No. 3. However, this value fell close to the outside of the analytical curve, and therefore the measuring conditions were adjusted (Measuring No. 4), whereby a measured value of 0.143 was obtained. The sample having an arsenic concentration of a 0.001 ppm order was incapable of detecting on any measuring conditions.

This application is based on Japanese Priority Application HEI 9-016425, filed with the Japanese patent office on Jan. 30, 1997, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A hydride formation analytical apparatus, comprising:
    a reagent-introducing part comprising an acid feeding section comprising a plurality of reservoirs in which acid is stored and a reducing agent feeding section comprising a plurality of reservoirs in which reducing agent is stored;
    a reaction part;
    a detecting part; and
    a control circuit connected to the acid feeding section and the reducing agent section of said reagent introducing part and to said detecting part; wherein said control circuit automatically controls the type and concentration of acid taken from said acid feeding section and the type and concentration of reducing agent taken from the reducing agent feeding section which are introduced into a sample in said reaction part to be analyzed and automatically controls the analysis of target compounds in said sample undergoing analysis.

2. The analytical apparatus as described in claim 1, further comprising:
    a computer connected to said control circuit.

3. The analytical apparatus as described in claim 1, wherein said detecting part comprises:
    a detecting instrument selected from the group consisting of an atomic absorption spectrophotometer, and an ICP emission spectral analyzer.

4. The analytical apparatus as described in claim 1, further comprising:
    a sample-introducing part; and
    a gas-liquid separating part;
    wherein said reaction part is connected to said sample-introducting part and said reagent introducing part, and said gas-liquid separating part is connected to said reaction part and said detecting part.

5. The analytical apparatus as described in claim 4, further comprising:
    an autosampler connected to said sample-introducing part.

6. The analytical apparatus as described in claim 4, further comprising:
    a preliminary reagent-introducing part; and
    a preliminary reaction part,
    wherein said preliminary reaction part is connected to said reaction part, and said preliminary reagent-introducing part is connected to said preliminary reaction part.

7. The analytical apparatus as described in claim 4, further comprising:
    a tube line; and
    a carrier liquid,
    wherein said tube line connects said sample-introducing part to said reaction part,
    connects said reagent-introducing part to said reaction part,
    connects said reaction part to said gas-liquid separation part, and connects said gas-liquid separation part to said detection part, wherein said carrier liquid transports compounds through said tube line.

8. The analytical apparatus as described in claim 4, wherein said sample-introduction part comprises:

a loop;

a hexagonal valve; and a tube line, wherein said loop and hexagonal valve are connected to said tube line, and said tube line is connected to said reaction part.

9. A hydride formation analytical apparatus, comprising:

a reagent-introducing part comprising an acid feeding section comprising a plurality of reservoirs in which acid is stored, a reducing agent feeding section comprising a plurality of reservoirs in which reducing agent is stored and a diluting water feeding section;

a reaction part;

a detecting part; and a control circuit connected to the acid feeding section and the reducing agent section of said reagent introducing part and to said detecting part; wherein said control circuit automatically controls the type and concentration of acid taken from said acid feeding section, the type and concentration of reducing agent taken from the reducing agent feeding section and the amount of diluting water taken from the diluting water feeding section which are introduced into a sample in said reaction part to be analyzed and automatically controls the analysis of target compounds in said sample undergoing analysis.

10. The analytical apparatus as described in claim 9, further comprising:

a computer connected to said control circuit.

11. The analytical apparatus as described in claim 9, wherein said detecting part comprises:

a detecting instrument selected from the group consisting of an atomic absorption spectrophotometer, an ICP atomic emission spectrometer and an ICP mass spectrometer.

12. The analytical apparatus as described in claim 9, further comprising:

a sample introducing part; and a gas-liquid separating part, wherein said reaction part is connected to said sample introducing part and said reagent introducing part, and said gas-liquid separating part is connected to said reaction part and said detecting part.

13. The analytical apparatus as described in claim 12, further comprising an autosampler connected to said sample introducing part.

14. The analytical apparatus as described in claim 12, further comprising:

a preliminary reagent introducing part; and a preliminary reaction part, wherein said preliminary reaction part is connected to said reaction part, and said preliminary reagent introducing part is connected to said preliminary reaction part.

15. The analytical apparatus as described in claim 12, further comprising:

a tube line; and a carrier liquid, wherein said tube line connects said sample introducing part to said reaction part, connects said reagent introducing part to said reaction part, connects said reaction part to said gas-liquid separation part, and connects said gas-liquid separation part to said detection part, wherein said carrier liquid transports compounds through said tube line.

16. The analytical apparatus as described in claim 12, wherein said sample introduction part comprises:

a loop;

a hexagonal valve; and a tube line, wherein said loop and hexagonal valve are connected to said tube line, and said tube line is connected to said reaction part.

* * * * *